(12) United States Patent
Norman

(10) Patent No.: US 7,796,264 B2
(45) Date of Patent: Sep. 14, 2010

(54) METHOD AND SYSTEM FOR ENHANCED REMOTE DETECTION OF LOW CONCENTRATION VAPORS

(75) Inventor: Jeffrey B. Norman, Newbury Park, CA (US)

(73) Assignee: The Boeing Company, Chicago, IL (US)

( * ) Notice: Subject to any disclaimer, the term of this patent is extended or adjusted under 35 U.S.C. 154(b) by 276 days.

(21) Appl. No.: 12/137,413

(22) Filed: Jun. 11, 2008

(65) Prior Publication Data

US 2009/0310130 A1 Dec. 17, 2009

(51) Int. Cl.
*G01N 21/00* (2006.01)
(52) U.S. Cl. ....................... 356/436; 356/437
(58) Field of Classification Search .......... 356/432–442
See application file for complete search history.

(56) References Cited

U.S. PATENT DOCUMENTS

| | | | | |
|---|---|---|---|---|
| 5,294,796 A * | 3/1994 | Fee | ........................ | 250/338.5 |
| 5,298,751 A * | 3/1994 | Fee et al. | .................. | 250/338.5 |
| 6,343,534 B1 | 2/2002 | Khanna et al. | | |
| 6,853,452 B1 | 2/2005 | Laufer | | |
| 6,895,804 B2 * | 5/2005 | Lovell et al. | ................ | 73/31.05 |
| 7,098,672 B2 * | 8/2006 | Belyakov et al. | ............. | 324/646 |
| 7,298,475 B2 * | 11/2007 | Gandhi et al. | ................ | 356/318 |
| 2007/0146716 A1 * | 6/2007 | Dudelzak et al. | ............. | 356/437 |

OTHER PUBLICATIONS

Aker, Pamela, "Optics & Infrared Sensing; Differential Remote Photoacoustic Spectroscopoy (DIRPAS)," Pacific Northwest National Laboratory. Feb. 2008.

Hecht, Jeff, "Active Denial Technology (ADT); Microwave beam weapon to disperse crowds," New Scientist. Oct. 24, 2001.

Janni, James et al., "Infrared absorption of explosive molecule vapors," Spectrochimica Acta Part A. 53 (1997) 1375-1381.

Leggett, Daniel C., et al., "Release of Explosive-Related Vapors from Land Mines," US Army Corps of Engineers. Feb. 2001 Technical Report ERDC/CRREL TR-01-6.

Pushkarsky, Michael B., et al., "High-sensitivity detection of TNT," PNAS. Dec. 2006; 103;52:19630-19634.

Seregelyi, JS, et al., "Neutralisation of Landmines Using a High-Power Mircrowave Applicator," Defence Research Establishments Ottawa & Suffield. Oct. 2001; Technical Report DRES-TR-01-127.

Welch, Gen. Larry D., et al., "Directed Energy Weapons," Defense Science Board, Task Force, Office of the Under Secretary of Defense, Dec. 2007.

* cited by examiner

*Primary Examiner*—Michael P Stafira

(57) ABSTRACT

There is provided a method for detecting a target material, preferably a solid or liquid target material. The method may comprise the steps of targeting a material for analysis, heating the material with a heating source from a remote distance to effectively increase a temperature of the material and to effectively increase a vapor pressure of the material in an environment adjacent to the material, measuring with a sensor the material vapor in the adjacent environment from the remote distance, and detecting the identity of the material using data generated during the measuring step. There is also provided a system for detecting a target material having a low vapor pressure comprising a first energy generating source, a sensor for measuring properties of gaseous materials from a standoff distance, the sensor producing data, and a computer for determining the target material based on the data produced by the sensor.

21 Claims, 3 Drawing Sheets

METHOD AND SYSTEM FOR ENHANCED REMOTE DETECTION OF LOW CONCENTRATION VAPORS

BACKGROUND OF THE DISCLOSURE

1) Field of the Disclosure

The disclosure relates to a method and system for enhanced remote detection of low concentration vapors, and more particularly to a method and system for enhanced remote detection of low concentration vapors using a heating source and a sensor.

2) Description of Related Art

There is an ongoing need for methods and systems capable of early remote detection of hazardous and controlled solid and liquid materials, such as chemical agents, biological agents, explosive agents, narcotics and other hazardous and controlled substances, and in particular, solid and liquid materials having very low vapor pressures. Every solid and liquid material has some vapor pressure, with solid materials typically having very low vapor pressures at ambient or room temperature, and liquid materials having higher vapor pressures at ambient or room temperature. In particular, explosive solid materials such as TNT (trinitrotoluene), have a very low vapor concentration at ambient or room temperature. Such low vapor concentrations can make detection, and in particular vapor detection, of such materials difficult. The detection of such hazardous solid and liquid materials is important for security screening measures, forensic analysis, and environmental applications. The choice of the detection method or system used depends on the chemical agent, biological agent, or explosive agent being sought, any expected background interferences, and whether point samples or standoff distances are required. Local, non-remote detection methods and systems using point samples for detecting hazardous solid and liquid vapor materials exist that use low power infrared, ultraviolet, or visible light sources to detect and identify vapor materials based on their unique optical signatures, such as emission, absorption, and scattering. These methods and systems are capable of detecting solid and liquid material vapors at trace levels at parts per billion concentration levels or lower. However, active (laser-based) and passive (solar or thermal based) remote vapor detection and identification of extremely low vapor pressure, such as parts per billion concentrations and lower, solid and liquid materials under ambient or near room temperature conditions is currently not feasible due to the small interaction (e.g. light absorption) between the vapor material and the sensor radiation. In the case of an active remote sensing system, an increase in vapor detection probability can be achieved by increasing the laser power at a fixed vapor concentration. However, for a photon shot noise limited laser sensor, such as one whose light signal is large enough that the sensor system noise depends primarily on the statistics of the photons entering the sensor receiver aperture and not on detector system electronic performance in the sensor, the signal-to-noise ratio (SNR) increases only as the square root of the laser power, so that doubling the laser power of such a sensor increases the SNR only by the square root of two, or about a factor of 1.4. This is a modest gain compared to the order of magnitude or more improvement required to remotely detect extremely low concentration vapors. SNR is a primary determinant of the minimum detectable vapor concentration and of the probability of vapor detection for a laser sensor. Continuing to increase laser power while maintaining other essential capabilities and properties of the laser sensor system, such as narrow spectral line width, wavelength tunability, compact size, or power efficiency, is a major challenge. Another known method uses a large receiver telescope aperture to collect more of the light reflected, scattered, or emitted from the target when implementing active and passive remote sensing techniques, thus increasing the SNR. However, such large receiver apertures limit the portability of remote sensors, thereby limiting the platforms on which they can be deployed, and such large apertures may also decrease the ability to be covert in certain applications. In addition, as for the laser power, the sensor signal increases only as the square root of the receiver aperture area. Another known method uses lower noise photodetection hardware, such as lower noise photodiodes or cryogenically cooled detectors. However, while lower noise photodetection systems may increase the sensitivity of remote sensors, ultimate sensitivity is determined by photon shot noise, and a system that is independent of the sensor itself may be needed to overcome this limitation to further increase the probability of detection. Another known method uses integration of the signal over long time periods and/or averaging of multiple signal samples. However, such signal integration and sample averaging over long periods may have the limitation that the target or intervening atmosphere may be dynamically changing on a time scale that is short compared to the integration or sampling time, thus degrading the time resolution of the measurement. Moreover, sample-to-sample signal correlations set a limit to the achievable enhancement using this system. Another known method uses reduction of the distance between the sensor and the target material by either moving the sensor closer to the target material or moving the target material closer to the sensor. However, significantly reducing sensor-to-target distance is often not possible, such as for airborne applications and in the detection of hazardous and non-cooperative targets. In those cases where decreasing the range is possible, the SNR increases only linearly with decreasing range under photon shot noise limited conditions, which may not provide enough signal enhancement for many applications requiring ultra high sensitivity.

In addition, vapor detection methods and systems are known that use lasers to detect the vapor signatures of hazardous solid and liquid materials. However, the performance of known vapor detection sensors are often limited by the low vapor concentration of many solid and liquid materials under ambient conditions and by the often long standoff distances between the sensor and the target material.

Existing methods and systems do not sufficiently enhance the SNR of the measurement to render the target solid and liquid materials detectable at all ranges of interest using existing remote sensor technology, and in particular, to render target solid and liquid materials having very low vapor pressures at ambient temperature detectable. Known methods and systems may typically only increase the SNR by a factor of between 1 and 2, rather than by a factor of 10 or more, which is typically what is needed to detect very low vapor pressure materials. Thus, the increase in sensor SNR for known methods and systems is linear or sub-linear with changes in remote sensor parameters only, such as radiation power or receiver aperture area. Moreover, existing methods and systems only seek to improve or change the sensor itself rather than change the conditions of the material target for the purpose of improving detection probability.

Accordingly, there is a need for a method and system for enhanced remote detection of low concentration vapors that provides advantages over known methods and systems.

SUMMARY OF THE DISCLOSURE

This need for a method and system for enhanced remote detection of low concentration vapors, as well as a unique, nonobvious, and advantageous method and system, is satisfied. None of the known methods and systems provide all of the numerous advantages discussed herein. Unlike known methods and systems, embodiments of the method and system may provide one or more of the following advantages: provides a method and system for detecting target materials such as hazardous solid and liquid materials, including chemical agents, biological agents, explosive agents, or other hazardous substances, by changing the conditions of the target materials for the purpose of improving detectability of such materials; provides a method and system for enhanced remote detection of low concentration vapors that more readily achieves performance improvements and increases vapor concentration by an order of magnitude or greater; provides a method and system that increases the probability of remote detection of a material vapor by effectively increasing the interaction between the material vapor and the sensor radiation to render the target materials detectable at all ranges of interest using existing remote sensor technology, where such enhancement makes it particularly valuable for the remote detection of target materials having very low ambient vapor pressures which can make the difference between a target material being undetectable and detectable; provides a method and system for enhanced remote detection of low concentration vapors that uses a heating source to heat the solid and/or liquid target materials from a remote or standoff distance, which in turn, increases the vapor pressure of the solid and/or liquid target materials, thereby increasing the vapor concentration of the surrounding environment, and that uses a passive and/or active remote sensing system to exploit the increased vapor concentration to substantially improve the probability of detection of the solid and/or liquid target materials; and, provides a method and system that may be used in security screening measures, law enforcement applications, forensic analysis, environmental applications, homeland security, military applications, and commercial applications.

In an embodiment of the disclosure, there is provided a method for detecting a material comprising the steps of: targeting the material for analysis; heating the material with a heating source from a remote distance to effectively increase a temperature of the material and to effectively increase a vapor pressure of the material in an environment adjacent to the material; measuring with a sensor a material vapor in the adjacent environment from the remote distance; and, detecting the identity of the material using data generated during the measuring step.

In another embodiment of the disclosure, there is provided a method of detecting a material having a low vapor pressure comprising the steps of: targeting the material for analysis; heating the material with a heating source from a standoff distance to effectively increase a temperature of the material and to effectively increase a vapor pressure of the material in an environment adjacent to the material; measuring with a sensor a material vapor in the adjacent environment from the standoff distance; and, detecting the identity of the material using data generated during the measuring step.

In another embodiment of the disclosure, there is provided a system for detecting a target material having a low vapor pressure comprising: a first energy generating source; a sensor for measuring properties of gaseous materials from a standoff distance, the sensor producing data; and, a computer for determining the target material based on the data produced by the sensor.

BRIEF DESCRIPTION OF THE DRAWINGS

The foregoing and other advantages and features, and the manner in which the same are accomplished, will become readily apparent upon consideration of the following detailed description taken in conjunction with the accompanying drawings which illustrate preferred and exemplary embodiments, but which are not necessarily drawn to scale, wherein.

DETAILED DESCRIPTION OF THE DISCLOSURE

Figure 1:
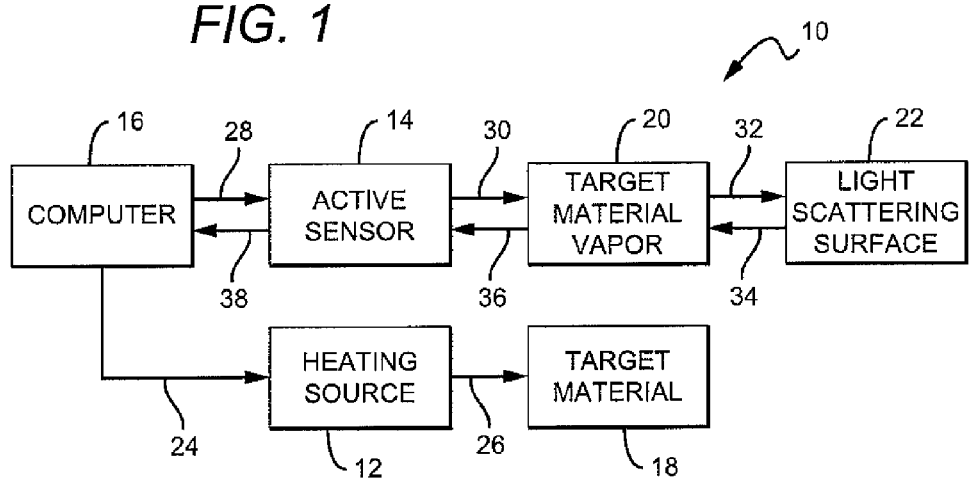
FIG. 1 is a block diagram of a first disclosed embodiment of the method and system.

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art.

The method and system of the disclosed embodiments may be used in connection with security screening measures, law enforcement applications, forensic analysis, environmental applications, homeland security, military applications, commercial applications, and various other applications involving the detection of solid and/or liquid materials or other substances. Accordingly, one of ordinary skill in the art will recognize and appreciate that the method and system of the disclosure can be used in any number of applications involving the detection of solid and/or liquid materials or other substances.

In an embodiment of the disclosure there is provided a method for detecting a material. The material detected may comprise an unknown or known solid or liquid target material, such as a hazardous liquid material, a hazardous solid material, an explosive related compound, an improvised explosive device (IED), a chemical agent, a biological agent, a hazardous environmental agent, pesticides, a controlled substance, or another suitable target material. The method comprises the step of targeting the material for analysis. The method further comprises the step of heating the material with a heating source from a remote or standoff distance to effectively increase the temperature of the material and to effectively increase the vapor pressure of the material in an environment adjacent to the material. For purposes of this application, the term "standoff distance" means a certain safety distance away from a hazardous solid or liquid material or target material that is mandated by a standard operating procedure. Depending on what the suspected target material is and on whether the target material is cooperative or non-cooperative, the standoff distance may be a few feet away from the target material or the standoff distance may be hundreds or thousands of feet away from the target material. The heating source may comprise a laser beam, a microwave beam, a millimeter wave beam, or one of various incoherent light sources, such as an infrared lamp or incandescent light source, or another suitable heating source. Preferably, the heating source comprises a high power microwave radiation beam, a millimeter wave beam, or an infrared laser beam which may be used at very long distances from the target material. The laser beam may be from a laser comprising a fiber laser, a solid state laser, a gas laser, a chemical laser, or another suitable laser type. The type of laser or other heating source used depends on various factors, such as the type of enclosure or substrate of the target material, how much moisture is in the surrounding material, whether there is sand or plastic present near the target material, what an object or device is made of that houses or makes up the target material, and various other factors. Preferably, the heating source uses electromagnetic radiation. Preferably, the target material is heated for an effective period of time to effectively increase the vapor pressure of the target material in an environment adjacent to the material. The length of time of heating depends on the type and power of the heating source used and the type of environment hosting the target material. Typically, the heating source may be applied to the target material for a short period of time, such as seconds or minutes, and the target material preferably does not need to be heated to a very high temperature. For example, depending on what the target material is, the target material may be heated from ambient or room temperature of 20 degrees C. to 25 degrees C. to a temperature of 40 degrees C. to 50 degrees C. However, the target material may be heated to higher suitable temperatures as well. Preferably, the amount of heat applied to the target material is sufficient to target the size or diameter of the material so that energy is not wasted. For example, if the target material is 1 cm (centimeter) in diameter, it is not efficient to shine a 1 m (meter) energy beam on the material because most of the energy would be wasted. Once the target material is sufficiently heated for an effective period of time, the vapor pressure of the material is increased, vapors emit from the target material into a volume accessible to the sensor, and the vapors have certain wavelengths at which they interact with the sensor radiation source, e.g., by linear light absorption or nonlinear optical interaction.

The method further comprises the step of measuring with a sensor the presence of a material vapor or vapor from the material, and potentially a quantity directly related to the vapor concentration, in the adjacent environment from the remote or standoff distance. When the vapor pressure of the target material is increased, the vapor concentration in the environment adjacent to the material increases. The sensor measures the material vapor and the increased vapor concentration in the adjacent environment. The sensor may comprise an active sensor, such as a laser based system, a passive sensor, such as a solar based or thermal based system, or another suitable sensor. Suitable active sensors that may be used may comprise a differential absorption light detection and ranging (DIAL) sensor, a coherent anti-Stokes Raman spectroscopy (CARS) sensor, a spontaneous Raman scattering sensor, a Laser Induced Fluorescence (LIF) sensor, an optical sensor, or other suitable active sensors. Active sensors may be used during the day and at night. Suitable passive sensors that may be used may comprise a hyperspectral imager, a multispectral imager, a thermal imager, or other suitable passive sensors. Passive sensors are preferably used during daylight hours. Preferably, the sensor uses electromagnetic radiation or energy. Preferably, the vapor concentration is increased by an order of magnitude or greater. The method further comprises the step of detecting the identity of the material using data generated during the measuring step. The data generated during the measuring step may be acquired and processed using a computer. Preferably, the data is generated via an automated system. For example, if a laser sensor is used, the laser is tuned with the computer, the light that is scattered or reflected back after passing through the vapor is detected, the resulting electronic signal is analyzed by a conventional computer program or customized computer software, and the material is identified and determined. The data output from the system may be reviewed by an operator of the system and appropriate steps may be taken depending on the material identified by the data output. The method may be used, among other things, to find out if a target material is active, that is, that the object being interrogated contains a sought after material, and to find out what the target material is within a device or object. The presence or absence of the target material within the device or object is typically unknown before heating and sensing it. A typical target material, such as TNT (trinitrotoluene), has a few parts per billion vapor pressure at room temperature. When TNT is heated from 25 degrees C. (room temperature) to 50 degrees C., there is about a 26 times increase in the vapor concentration. The actual factor by which the probability of detection increases for a given increase in vapor concentration depends on the sensor noise level, on the vapor concentration prior to heating of the target material, and on the detection threshold chosen by the sensor operator. As an example, for a remote sensor using the technique of differential absorption light detection and ranging (DIAL), the measured quantity is the product of the vapor concentration and the path length of the laser beam through the vapor. If the detection threshold is chosen such that the probability of false alarms is 1% and the probability of vapor detection is 50%, then an increase by a factor of ten (10) in vapor concentration, while keeping the laser beam path length through the vapor the same, increases the probability of detection to essentially 100% while keeping the false alarm rate at 1%. By measuring the increased vapor concentration and generating the data from such measuring step, the identity of the material can be determined based on such data from the material vapor and vapor concentration measuring step.

Referring now to the drawings, FIG. 1 is a block diagram of a first disclosed embodiment 10 of the method with a heating source and an active sensor. FIG. 1 shows a heating source 12, an active sensor 14, a computer 16, a target material 18, a target material vapor 20, and a light scattering surface 22. The computer 16 initiates a heating beam generator control signal 24, such as a microwave generator control signal, to the heating source 12. The heating source 12, such as a high power microwave beam generator, heats the target material 18 with a heating beam 26, such as a microwave beam. The heating source 12 heats the target material 18 for an effective period of time so that the temperature of the target material increases and the vapor pressure of the target material increases. The target material vapor 20 is emitted from the target material 18 upon heating. The computer 16 initiates a control and sensor signal 28, such as a laser control, to activate the active sensor 14. The active sensor 14, such as a differential absorption light detection and ranging (DIAL) sensor, generates an interrogating light beam 30, such as a laser light beam, directed at the target material vapor 20. A light beam transmission 32 through the target material vapor 20 travels to the light scattering surface 22. A portion of the scattered light 34 travels back through the target material vapor 20. A scattered light transmission 36 through the target material vapor travels back to the active sensor 14. A sensor signal 38 travels back to the computer 16. The computer analyzes and generates the vapor concentration measurement data gathered from the sensor to detect the identity of the target material.

Figure 2:
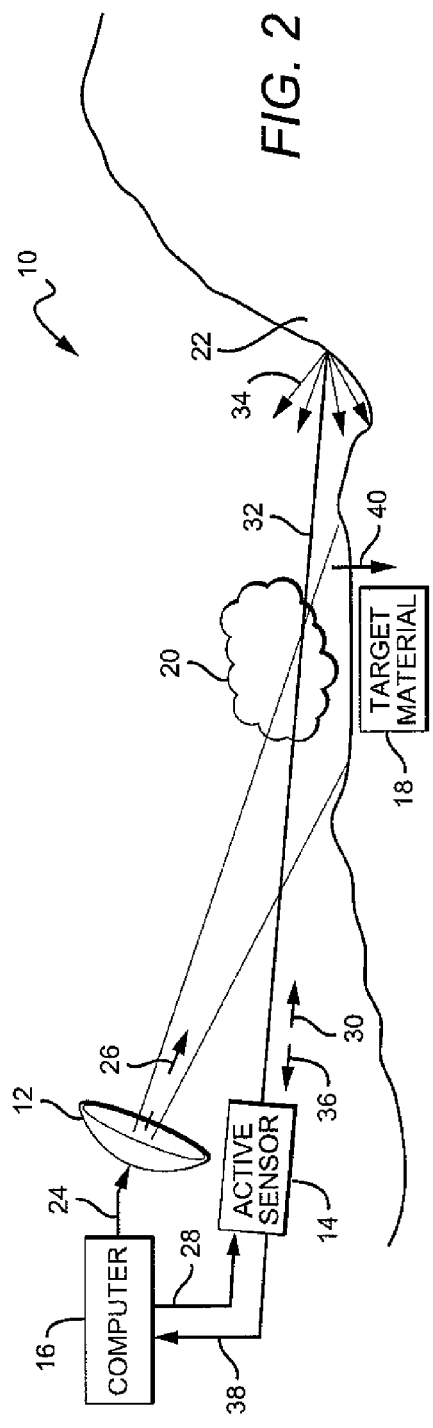
FIG. 2 is a schematic diagram of the first disclosed embodiment of the method and system.

FIG. 2 is a schematic diagram of the first disclosed embodiment 10 of the method. FIG. 2 shows the heating source 12, the active sensor 14, the computer 16, the target material 18, the target material vapor 20, and the light scattering surface 22. The computer 16 initiates the heating beam generator control signal 24, such as a microwave generator control signal, to the heating source 12. The heating source 12, such as a high power microwave beam generator, heats the target material 18 with the heating beam 26, such as a microwave beam. The heating source 12 heats the target material 18 for an effective period of time so that the temperature of the target material increases and the vapor pressure of the target material increases in the environment adjacent to the target material. The target material vapor 20 is emitted from the target material 18 upon heating. Absorbed energy 40 from the heating source is absorbed into the target material 18. The computer 16 initiates the control and sensor signal 28, such as a laser control, to activate the active sensor 14. The active sensor 14, such as a differential absorption light detection and ranging (DIAL) sensor, generates the interrogating light beam 30, such as a laser light beam, directed at the target material vapor 20. The light beam transmission 32 through the target material vapor 20 travels to the light scattering surface 22. A portion of the scattered light 34 travels back through the target material vapor 20. The scattered light transmission 36 through the target material vapor travels back to the active sensor 14. The sensor signal 38 travels back to the computer 16. The computer analyzes and generates the vapor concentration measurement data gathered from the sensor to detect the identity of the target material.

Figure 3:
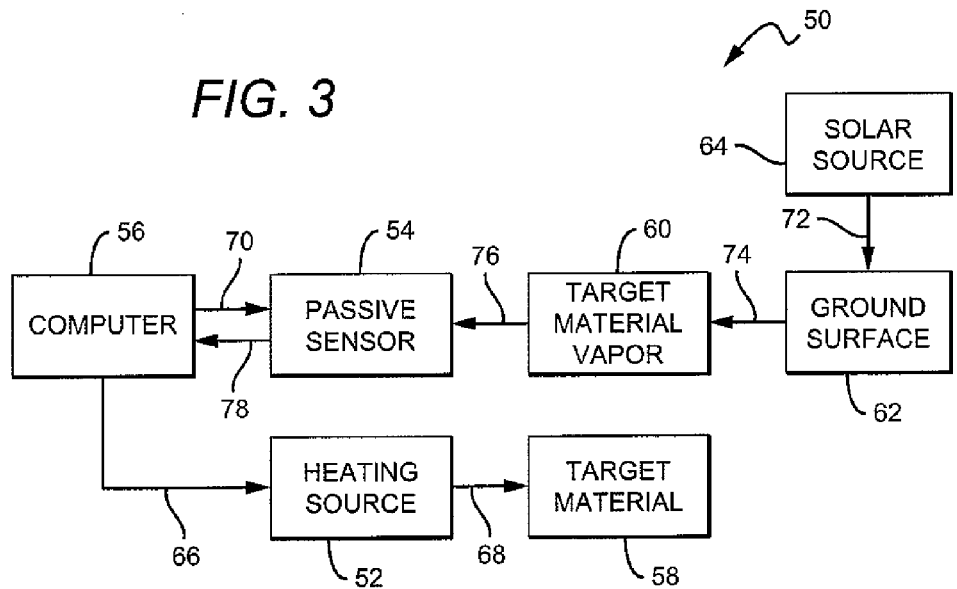
FIG. 3 is a block diagram of a second disclosed embodiment of the method and system.

FIG. 3 is a block diagram of a second disclosed embodiment 50 of the method with a heating source and a passive sensor. FIG. 3 shows a heating source 52, a passive sensor 54, a computer 56, a target material 58, a target material vapor 60, a ground surface 62, and a solar source 64. The computer 56 initiates a heating beam generator control signal 66, such as a high power infrared laser signal, to the heating source 52. The heating source 52, such as a high power infrared laser, heats the target material 58 with a heating beam 68, such as an infrared laser beam. The heating source 52 heats the target material 58 for an effective period of time so that the temperature of the target material increases and the vapor pressure of the target material increases. The target material vapor 60 is emitted from the target material 58 upon heating. The computer 56 initiates a control and sensor signal 70 to activate the passive sensor 54. The solar source 64, such as the sun, emits solar radiation 72 to the ground surface 62. Scattered solar radiation 74 from the ground surface 62 travels to the target material vapor 60. Scattered solar radiation transmission 76 transmitted through the target material 60 travels to the passive sensor 54. The passive sensor 54, such as a hyperspectral imager sensor, detects the scattered solar radiation transmission 76 transmitted through the target material vapor 60. A sensor signal 78 travels back to the computer 56. The computer analyzes and generates the vapor concentration measurement data and vapor spectral signature data gathered from the sensor to detect the identity of the target material.

Figure 4:
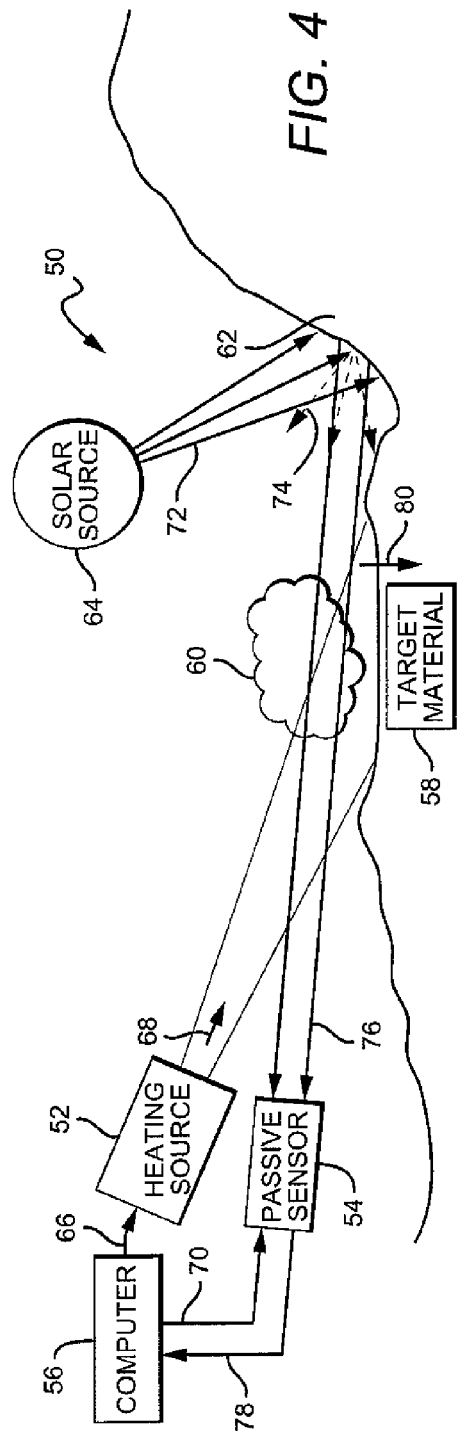
FIG. 4 is a schematic diagram of the second disclosed embodiment of the method and system; and, FIG. 5 is a graph illustrating the vapor concentrations of various explosive agents.

FIG. 4 is a schematic diagram of the second disclosed embodiment 50 of the method. FIG. 4 shows the heating source 52, the passive sensor 54, the computer 56, the target material 58, the target material vapor 60, the ground surface 62, and the solar source 64. The computer 56 initiates the heating beam generator control signal 66, such as a high power infrared laser signal, to the heating source 52. The heating source 52, such as a high power infrared laser, heats the target material 58 with the heating beam 68, such as an infrared laser beam. The heating source 52 heats the target material 58 for an effective period of time so that the temperature of the target material increases and the vapor pressure of the target material increases in the environment adjacent the target material. The target material vapor 60 is emitted from the target material 58 upon heating. Absorbed energy 80 from the heating source is absorbed into the target material 18. The computer 56 initiates the control and sensor signal 70 to activate the passive sensor 54. The solar source 64, such as the sun, emits the solar radiation 72 to the ground surface 62. A portion of the scattered solar radiation 74 from the ground surface 62 travels to the target material vapor 60. The scattered solar radiation transmission 76 transmitted through the target material vapor 60 travels to the passive sensor 54. The passive sensor 54, such as the hyperspectral imager sensor, detects the scattered solar radiation transmission 76 transmitted through the target material vapor 60. The sensor signal 78 travels back to the computer 56. The computer analyzes and generates the vapor concentration measurement data and vapor spectral signature data gathered from the sensor to detect the identity of the target material.

Figure 5:
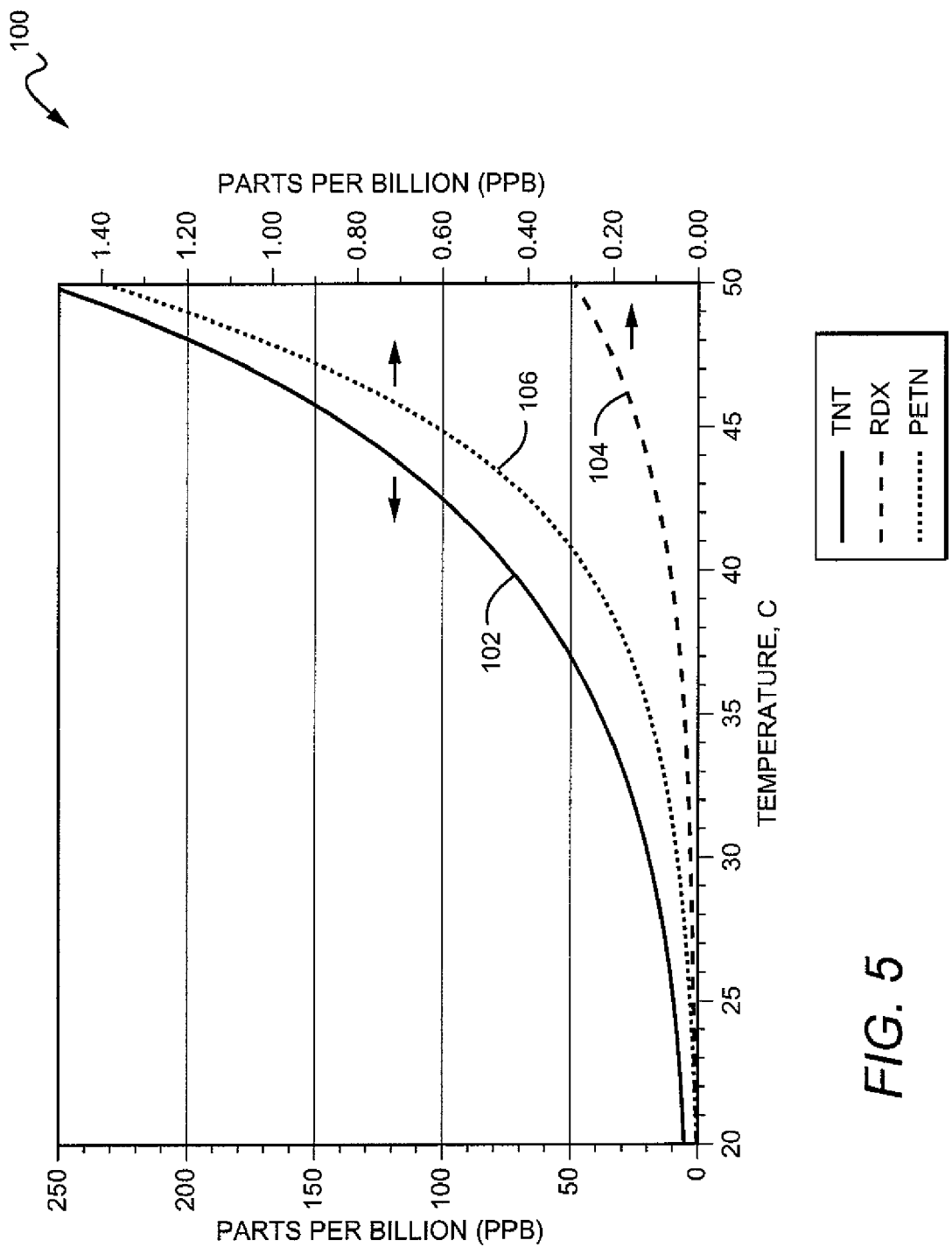

FIG. 5 is a graph 100 illustrating the vapor concentration of various explosive agents. The x-axis shows the temperature in Celsius. The y-axis shows concentration in parts per billion units. The explosives include TNT (trinitrotoluene) as indicated on the graph as reference number 102, RDX (cyclotrimethylenetrinitramine) as indicated on the graph as reference number 104, and PETN (pentaerythritol tetranitrate) as indicated on the graph as reference number 106. For TNT, the equilibrium vapor concentration increases by approximately 26 times from 25 degrees C. (room temperature) to 50 degrees C. For RDX, the equilibrium vapor concentration increases by approximately 48 times from 25 degrees C. (room temperature) to 50 degrees C. For PETN, the equilibrium vapor concentration increases by approximately 77 times from 25 degrees C. (room temperature) to 50 degrees C. Thus, the graph shows that dramatic increases in vapor pressure may be achieved in these explosive materials with modest temperature increases.

In another embodiment of the disclosure, there is provided a method of detecting a material having a low vapor pressure. The material detected may comprise an unknown or known solid or liquid target material, such as a hazardous solid or liquid material, an explosive related compound, an improvised explosive device (IED), a chemical agent, a biological agent, a hazardous environmental agent, pesticides, a controlled substance, or another suitable solid or liquid material. The method comprises the step of targeting the material for analysis. The method further comprises the step of heating the material with a heating source from a standoff or remote distance to effectively increase the temperature of the material and to effectively increase the vapor pressure of the material in an environment adjacent to the material. The method further comprises the step of measuring with a sensor the presence of a material vapor or vapor of the material, and preferably the vapor concentration, in the adjacent environment from the standoff or remote distance. The method further comprises the step of detecting the identity of the material using data generated during the measuring step. The heating source may comprise a laser beam, a microwave beam, a millimeter wave beam, one of various incoherent light sources, such as an infrared lamp or incandescent light source, or another suitable heating source. The sensor may comprise an active sensor, such as a laser based system, or a passive sensor, such as a solar based or thermal based system, or another suitable sensor. Suitable active sensors that may be used may comprise a differential absorption light detection and ranging (DIAL) sensor, a coherent anti-Stokes Raman spectroscopy (CARS) sensor, a spontaneous Raman scattering sensor, a Laser Induced Fluorescence (LIF) sensor, an optical sensor, or other suitable active sensors. Suitable passive sensors that may be used may comprise a hyperspectral imager, a multispectral imager, a thermal imager, or other suitable passive sensors. Preferably, the vapor concentration is increased by an order of magnitude or greater.

In another embodiment of the disclosure there is provided a system for detecting a target material having a low vapor pressure. The target material may comprise an unknown or known solid or liquid target material, such as a hazardous solid or liquid material, an explosive related compound, an improvised explosive device (IED), a chemical agent, a biological agent, a hazardous environmental agent, pesticides, a controlled substance, or another suitable target material. The system comprises a first energy generating source. The first energy generating source may comprise a laser beam, a microwave beam, a millimeter wave beam, one of various incoherent light sources, such as an infrared lamp or incandescent light source, or another suitable energy generating source. The first energy generating source heats the target material to be detected, thereby increasing a vapor pressure of the target material in an environment adjacent to the target material. The system further comprises a sensor for measuring properties of gaseous materials from a standoff distance, the sensor producing data. The sensor may comprise an active sensor, such as a laser based system, or a passive sensor, such as a solar based or thermal based system, or another suitable sensor. Suitable active sensors that may be used may comprise a differential absorption light detection and ranging (DIAL) sensor, a coherent anti-Stokes Raman spectroscopy (CARS) sensor, a spontaneous Raman scattering sensor, a Laser Induced Fluorescence (LIF) sensor, an optical sensor, or other suitable active sensors. Suitable passive sensors that may be used may comprise a hyperspectral imager, a multispectral imager, a thermal imager, or other suitable passive sensors. Preferably, the gaseous materials the sensor measures include the material vapor or vapor of the material, and the vapor concentration of the material in an environment adjacent to the material. The system further comprises a computer for determining the material based on the data produced by the sensor.

The method and system of the disclosure provides a hybrid system having a heating system and a sensing system. The heating system is capable of heating a target material from a remote or standoff location using a heating source or energy source that generates and directs a beam of electromagnetic radiation, such as a laser beam, a microwave beam, a millimeter wave beam, one of various incoherent light sources, such as an infrared lamp or incandescent light source, or another suitable energy generating source, at the target material of interest with the appropriate power, frequency, divergence, spot size, or other properties to effectively heat the target material and significantly increase its vapor pressure and vapor concentration. The sensing system uses a remote or standoff sensor, such as an active or passive sensor, that uses electromagnetic radiation or energy to detect the material vapor and increased vapor concentration, thereby significantly increasing the probability of detection and identification of the target material. The sensing system detects and identifies the heated target material using the target material vapor pressure and established signal processing techniques. The increased vapor concentration significantly increases the probability of remote detection and identification of a vapor material by increasing the interaction, such as linear or non-linear optical interaction, of the sensor radiation with the vapor. The method and system of the disclosure takes advantage of the rapid increase in vapor pressure of many liquid and solid materials with an increase in temperature. For example, the vapor pressures of many solid explosive materials, such as TNT (trinitrotoluene), increase by about a factor of two for every five degree centigrade temperature rise. This corresponds to a concentration increase of nearly an order of magnitude for only a 15 degree temperature increase. Similar behavior is found in other hazardous substances. In addition, the light signal level for some active remote sensing techniques, such as coherent anti-Stokes Raman spectroscopy (CARS) sensors, depends on the square of the vapor concentration, which leads to a factor of 100 or more in increased signal for modest heating. The method and system of the disclosure increase the probability of vapor detection by increasing the vapor concentration relative to the fixed sensor concentration threshold. The method and system combine the technologies of a heating source and a sensor to achieve a significant increase in the probability of detection. The method and system may also be readily adaptable to a fielded application on mobile platforms using existing systems.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for detecting a material comprising the steps of:
    targeting the material for analysis;
    heating the material with a heating source from a remote distance to effectively increase a temperature of the material and to effectively increase a vapor pressure of the material in an environment adjacent to the material;
    measuring with a separate laser based active sensor a material vapor in the adjacent environment from the remote distance, wherein the laser based active sensor can measure the material vapor during daylight and at night; and,
    detecting the identity of the material using data generated during the measuring step.

2. The method of claim 1, wherein the heating source is selected from the group consisting of a laser beam, a microwave beam, a millimeter wave beam, an incoherent light source, an infrared lamp, and an incandescent light source.

3. The method of claim 2, wherein the laser beam is from a laser selected from the group consisting of a fiber laser, a solid state laser, a gas laser, and a chemical laser.

4. The method of claim 1, wherein the heating source uses electromagnetic radiation.

5. The method of claim 1, wherein the laser based active sensor is selected from the group consisting of a differential absorption light detection and ranging (DIAL) sensor, a coherent anti-Stokes Raman spectroscopy (CARS) sensor, a spontaneous Raman scattering sensor, and a Laser Induced Fluorescence (LIF) sensor.

6. The method of claim 1, wherein the laser based active sensor uses a laser-based source of electromagnetic radiation.

7. The method of claim 1, wherein the laser based active sensor measures a vapor concentration of the material in the adjacent environment, and further wherein the vapor concentration is increased by an order of magnitude or greater.

8. The method of claim 1, wherein the material is a solid or liquid material selected from the group consisting of a hazardous liquid material, a hazardous solid material, an explosive related compound, an improvised explosive device (IED), a chemical agent, a biological agent, a hazardous environmental agent, pesticides, and a controlled substance.

9. The method of claim 1, wherein the data generated during the measuring step is generated using a computer.

10. A method of detecting a material having a low vapor pressure comprising the steps of:
targeting the material for analysis;
heating the material with a heating source from a standoff distance to effectively increase a temperature of the material and to effectively increase a vapor pressure of the material in an environment adjacent to the material;
providing solar radiation from a separate solar source, wherein the solar radiation is scattered or reflected off of a ground surface, and further wherein a portion of the scattered or reflected solar radiation is transmitted through a material vapor;
detecting with a separate passive sensor the scattered or reflected solar radiation that is transmitted through the material vapor to the passive sensor; and,
detecting the identity of the material using data gathered from the passive sensor.

11. The method of claim 10, wherein the heating source is selected from the group consisting of a laser beam, a microwave beam, a millimeter wave beam, an incoherent light source, an infrared lamp, and an incandescent light source.

12. The method of claim 10, wherein the passive sensor is selected from the group consisting of a a hyperspectral imager and a multispectral imager.

13. The method of claim 10, wherein the data comprises vapor identification and concentration measurement data and vapor spectral signature data gathered from the passive sensor.

14. The method of claim 10, wherein the material is a solid or liquid material selected from the group consisting of an explosive related compound, an improvised explosive device (IED), a chemical agent, a biological agent, a hazardous environmental agent, pesticides, and a controlled substance.

15. A system for detecting a target material having a low vapor pressure comprising:
a target material;
a heating source for heating the target material, the heating source selected from the group consisting of a laser beam, a microwave beam, a millimeter wave beam, an incoherent light source, an infrared lamp, and an incandescent light source;
a separate laser based active sensor for measuring properties of gaseous materials from a standoff distance, the laser based active sensor producing data and being capable of measuring properties of the gaseous materials during daylight and at night; and,
a computer for determining the target material based on the data produced by the laser based active sensor.

16. The system of claim 15, wherein the laser based active sensor is selected from the group consisting of a differential absorption light detection and ranging (DIAL) sensor, a coherent anti-Stokes Raman spectroscopy (CARS) sensor, a spontaneous Raman scattering sensor, and a Laser Induced Fluorescence (LIF) sensor.

17. The system of claim 15, wherein the target material is a solid or liquid material selected from the group consisting of an explosive related compound, an improvised explosive device (IED), a chemical agent, a biological agent, a hazardous environmental agent, pesticides, and a controlled substance.

18. The system of claim 15, wherein the heating source heats the target material to be detected, thereby increasing a vapor pressure of the target material in an environment adjacent to the target material.

19. The system of claim 15, wherein the laser based active sensor measures a target material vapor in an environment adjacent to the target material, and wherein the laser based active sensor identifies a vapor and measures a vapor concentration of the target material in the environment adjacent to the target material.

20. A system for detecting a target material having a low vapor pressure comprising:
a target material;
a heating source for heating the target material, the heating source selected from the group consisting of a laser beam, a microwave beam, a millimeter wave beam, an incoherent light source, an infrared lamp, and an incandescent light source;
a separate solar source for providing solar radiation, wherein the solar radiation is scattered or reflected off of a ground surface, and further wherein a portion of the scattered or reflected solar radiation is transmitted through a target material vapor;
a separate passive sensor for detecting the scattered or reflected solar radiation that is transmitted through the target material vapor to the passive sensor; and,
a computer for detecting the identity of the target material by using data gathered from the passive sensor.

21. The system of claim 20, wherein the passive sensor is selected from the group consisting of a hyperspectral imager and a multispectral imager.

* * * * *